United States Patent
Ratron et al.

(10) Patent No.: US 9,358,119 B2
(45) Date of Patent: Jun. 7, 2016

(54) GLENOID COMPONENT WITH OFFSET CENTER AND ASSOCIATED METHODS

(71) Applicant: Tornier SAS, Montbonnot-Saint-Martin (FR)

(72) Inventors: Yves-Alain Ratron, Grenoble (FR); Robert J. Ball, West Olive, MI (US)

(73) Assignee: Tornier SAS (FR)

( * ) Notice: Subject to any disclaimer, the term of this patent is extended or adjusted under 35 U.S.C. 154(b) by 152 days.

(21) Appl. No.: 14/229,459

(22) Filed: Mar. 28, 2014

(65) Prior Publication Data

US 2014/0214170 A1 Jul. 31, 2014

Related U.S. Application Data

(62) Division of application No. 12/953,971, filed on Nov. 24, 2010, now Pat. No. 8,721,727.

(60) Provisional application No. 61/263,994, filed on Nov. 24, 2009.

(51) Int. Cl.
*A61F 2/40* (2006.01)
*A61F 2/30* (2006.01)

(52) U.S. Cl.
CPC .............. *A61F 2/4081* (2013.01); *A61F 2/40* (2013.01); *A61F 2002/30654* (2013.01); *A61F 2002/30884* (2013.01)

(58) Field of Classification Search
CPC ..................................................... A61F 2/4081
See application file for complete search history.

(56) References Cited

U.S. PATENT DOCUMENTS

| | | |
|---|---|---|
| 5,800,551 A | 9/1998 | Williamson et al. |
| 6,364,910 B1 | 4/2002 | Shultz et al. |
| 6,699,289 B2 | 3/2004 | Iannotti et al. |
| 7,713,306 B2 | 5/2010 | Gibbs |
| 8,721,727 B2 * | 5/2014 | Ratron .................. A61F 2/4081 623/19.13 |
| 2007/0244564 A1 | 10/2007 | Ferrand et al. |

* cited by examiner

*Primary Examiner* — Thomas J Sweet
*Assistant Examiner* — Megan Wolf
(74) *Attorney, Agent, or Firm* — Knobbe Martens Olson & Bear LLP

(57) ABSTRACT

A glenoid component having an offset center of articulation and associated systems and methods.

18 Claims, 2 Drawing Sheets

GLENOID COMPONENT WITH OFFSET CENTER AND ASSOCIATED METHODS

CROSS REFERENCE TO RELATED APPLICATIONS

This application is a divisional of U.S. patent application Ser. No. 12/953,971, filed on Nov. 24, 2010, now U.S. Pat. No. 8,721,727, entitled "Glenoid Component with Offset Center and Associated Methods," which claims the benefit under 35 U.S.C. §119 of U.S. Provisional Application No. 61/263,994, filed on Nov. 24, 2009, entitled "Glenoid Component with Offset Center," the disclosures of which are incorporated herein by reference in their entireties for all purposes.

BACKGROUND

Glenoid components generally include a body with two, opposing faces—a first face designed to articulate with either a natural or a prosthetic head of a humerus, and a second face designed to be pressed against the glenoid cavity of a shoulder blade and to be immobilized therein. The first face typically includes a spherical joint surface while the second face is provided with a fin, one or more pegs, or other means for anchoring the component into the bone forming the glenoid cavity.

The two faces of glenoid components are typically designed to be centered on one and the same geometric axis, that axis corresponding to the direction of implantation of the glenoid component into the glenoid cavity. In other words, the spherical joint surface is geometrically centered on a point belonging to the geometric axis and the fin or central anchoring peg, for example, are also centered on the geometric axis.

SUMMARY

Some embodiments relate to a glenoid component having anti-dislocation action in a periphery of a body of the component. In some embodiments, the glenoid component has an offset center.

Some embodiments relate to a method of repairing a shoulder joint of a patient, the method including exposing a glenohumeral joint, the glenohumeral joint including a humerus and a glenoid. A glenoid component is implanted into the glenoid, the glenoid component having a body and an anchor portion, the body defining an articulation surface and an anchor surface opposite the articulation surface. The anchor portion is centered on the body along a central axis of the glenoid component, where the articulation surface is curved and has an apical portion that is offset in a first direction from a central axis of the implant and a raised peripheral portion offset in a second direction from the central axis of the implant, the second direction being opposite the first direction. A humeral head is engaged with the articulation surface such that the humeral head is seated against the apical portion of the articulation surface when the humeral head is in a neutral position. The humeral head is articulated against the articulation surface from the neutral position to a modified position such that the humeral head transitions from the apical portion toward the raised peripheral portion to assess a risk of luxation between the humeral head and the glenoid component when the humeral head is moved toward the modified position.

Some embodiments relate to a method of replacing a glenohumeral joint including engaging a humeral head with an articulation surface of a glenoid component in a first, neutral position such that the humeral head is positioned against a center of articulation that is offset from a central axis of the glenoid component. The central axis is defined at an intersection of first and second mid-planes of the glenoid component that are orthogonal to one another. The method also includes articulating the humeral head to a second position such that the humeral head is engaged with a peripheral portion of the articulation surface that is raised relative to the center of articulation and offset from the central axis in an opposite direction than the center of articulation such that a tension in the glenohumeral joint retaining the humeral head against the articulation surface is increased.

Still other embodiments relate to a glenoid component including a body forming an articulation surface configured for engaging a humeral head and an anchor surface configured for engaging a glenoid cavity of a shoulder. The body has a first mid-plane, a second mid-plane orthogonal to the first mid-plane, and a central axis at an intersection of the first and second mid-planes. The articulation surface is substantially concave and defines a center of articulation and a raised peripheral portion, the center of articulation being located at an apical portion of the articulation surface and offset from both the first and second mid-planes in a first direction from the central axis. The raised peripheral portion is offset from the first and second mid-planes in a second direction that is opposite to the first direction. The glenoid component also includes an anchor portion connected to the body and centered on the central axis, the anchor portion being configured for being embedded in a boney structure of the glenoid cavity.

This summary is not meant to be limiting in nature. While multiple embodiments are disclosed herein, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
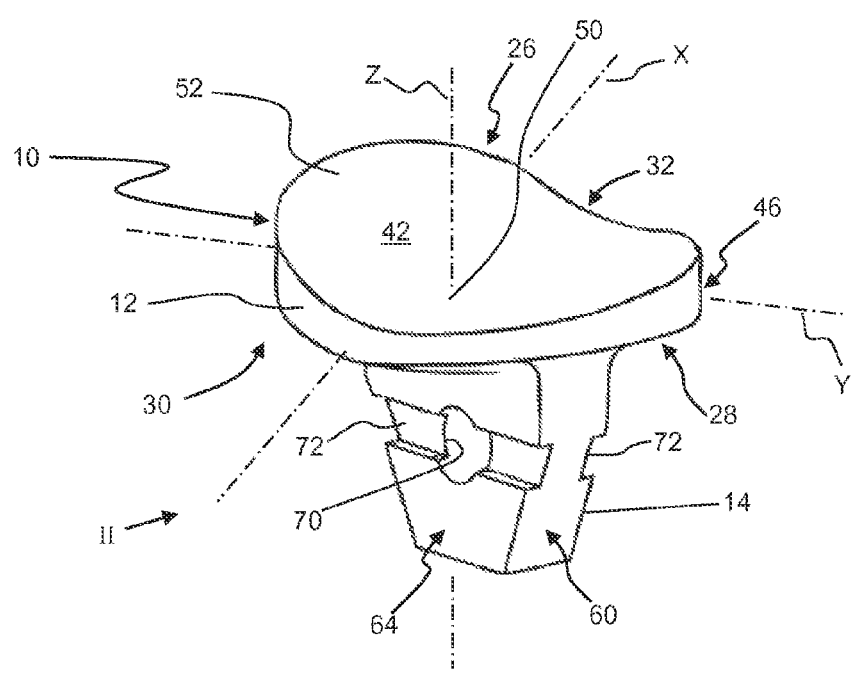
FIG. 1 is a perspective view of a glenoid component, according to some embodiments.

Various embodiments have been shown by way of example in the drawings and are described in detail below. As stated above, the intention, however, is not to limit the invention by providing such examples.

DETAILED DESCRIPTION

Various embodiments relate to reducing a risk of premature loosening of glenoid components from the glenoid cavity over time that is caused by repeated eccentric loading of the glenoid component—also described as a "rocking horse" effect. Some embodiments include a glenoid component having an offset center that raises an edge of the glenoid component relative to a remainder of the glenoid component. In some embodiments, the raised edge is selected in an area where a humeral head has a natural tendency to sub-luxate, the raised edge thereby helping to re-center the humeral head onto a center of articulation of the glenoid component.

Figure 2:
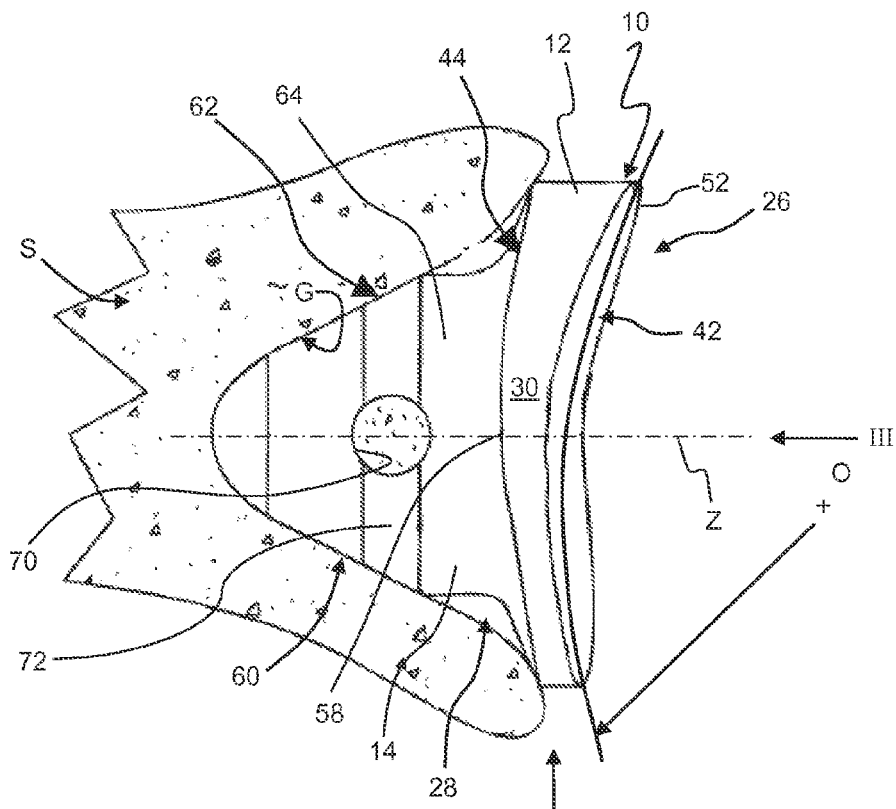
FIG. 2 is a first elevation view of the glenoid component of FIG. 1 implanted in the glenoid cavity of a shoulder blade that is shown in transverse section, according to some embodiments.
Figure 3:
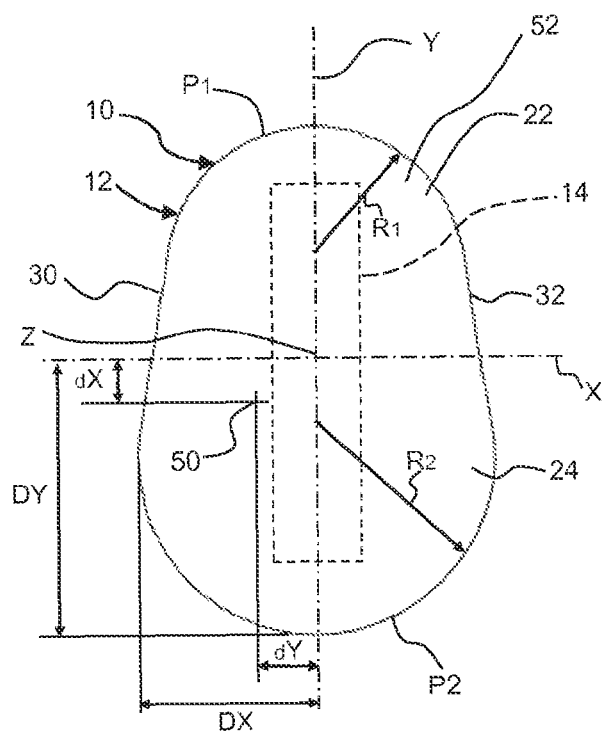
FIG. 3 is an elevation view of the glenoid component corresponding to perspective III of FIG. 2, according to some embodiments.

FIG. 1 is a perspective view of a glenoid component 10 and FIG. 2 is a view of the glenoid component 10 implanted in a glenoid G of a patient, according to some embodiments. As shown in FIGS. 1 and 2, the glenoid component 10 includes a body 12 and an anchor portion 14. FIG. 3 is an elevation view of the glenoid component 10 from perspective III of FIG. 2, according to some embodiments. As shown in FIG. 3, the body 12 has an upper portion 22 and a lower portion 24. As shown in FIGS. 1 and 2, the body 12 also includes a humeral side 26, a glenoid side 28, an anterior side 30, and a posterior side 32. The body 12 is optionally multiple pieces or a single, unitary piece, as desired. The body 12 is optionally formed of materials having rigidity and mechanical strength suitable for articulating with a natural or artificial humeral head and for being secured to the glenoid cavity G of a scapula S (FIG. 2).

As shown in FIG. 3, the body 12 defines an antero-posterior mid-plane X between the upper and lower portions 22, 24 and a vertical mid-plane Y between the first and second sides 30, 32, the mid-planes X, Y intersecting to form a central axis Z, also described as a geometric axis of the component 10 or implant axis of the component 10. The body 12 defines a first surface 42 at the humeral side 26 and a second surface 44 at the glenoid side 28 of the body 12, as well as an outer surface 46 extending about the body 12.

As shown, the first surface 42, also described as an articular surface, is generally curved overall and defines a center of articulation 50, as well as a periphery 52, also described as a peripheral portion. In some embodiments, the first surface 42 is sized, shaped, and/or otherwise configured to be articulated with a complementary surface of a natural or artificial humeral head (not shown). In general terms, the first surface 42 is substantially spherical and defines a geometric center O shown in FIG. 2. As shown in FIGS. 1-4, the first surface 42 optionally occupies most, or substantially all of the humeral side 26 of the body 12.

As shown in FIGS. 1 and 2, the first surface 42 is substantially concave and the center of articulation 50 corresponds to an apical portion of the concavity of the first surface 42. In other embodiments, the first surface 42 is substantially convex and the center of articulation 50 corresponds to an apical portion of the convexity of the first surface 42. As shown in FIGS. 1 and 3, the center of articulation 50 is offset from the axis Z such that the center of articulation 50 is not equidistant from the periphery 52 along the direction of either mid-plane X, Y. In some embodiments, the center of articulation 50 is offset from the antero-posterior mid-plane X toward the lower portion 24 and from the vertical mid-plane Y toward the anterior side 30 of the component 10.

As described in greater detail, by offsetting the center of articulation 50 from the central axis Z, the component 10 helps compensate for "rocking," or repeated, eccentric forces that can otherwise dislocate the component 10 from the glenoid G over time. Although FIG. 3 depicts the center of articulation 50 offset toward the anterior side 30 and the lower portion 24, the center of articulation 50 is optionally offset from the axis Z toward other portions of the component 10 (e.g., toward the upper portion 22 and posterior side 32).

As shown in FIG. 2, the second surface 44 of the body 12, also described as an anchoring or bearing surface, is also generally curved overall. In some embodiments, the second surface 44 is sized, shaped, and/or otherwise configured to be secured to the glenoid cavity G as shown in FIG. 2. For example, the second surface 44 is optionally substantially convex and configured to press against a surface of the glenoid cavity G that faces toward the humerus, where the second surface 44 defines a central region 58 at an apical portion of its convexity. Although the second surface 44 is shown as being substantially convex, in other embodiments the second surface 44 is substantially planar or concave, for example.

As shown in FIG. 3, according to some embodiments, a transverse projection of the body 12 relative to the axis Z is substantially symmetrical about the mid-planes X, Y, where the upper and lower portions 22, 24 of the body 12 include semi-circular portions P1, P2 with respective radii of curvature $R_1$, $R_2$, each of which have origins on the mid-plane Y. As shown, in transverse projection, the outer profile of the first surface 42 is in the overall shape of a pear and symmetric with respect to the mid-plane Y. In some embodiments, the overall, pear shape of the component 10 is substantially similar to an anatomical shape, or contour of an unimpaired glenoid cavity G such that the second surface 44 of the body 12 is configured to be secured to the glenoid cavity G with the body 12 generally fitting the outer contour of the cavity G.

As shown, the center of articulation 50 is offset with respect to the axis Z, anatomically forward (anterior) and downward (inferior) on the glenoid component 10 as configured in the glenoid cavity G following implantation. In particular, according to some embodiments, upon implantation of the component 10, the mid-plane X runs in a substantially antero-posterior anatomical direction and the mid-lane Y runs in a substantially vertical, or infero-superior anatomical direction, while the axis Z projects into the glenoid cavity G and scapula S in the direction of implantation of the component 10 in the glenoid cavity G. In other words, the center of articulation 50 belongs to an infero-anterior quadrant of the body 12. In turn, a superio-posterior portion of the first surface 42 is generally raised, or elevated, in comparison with a remainder of the body 12 in the direction of the axis Z. In other words, the periphery 52 is raised in the upper portion 22 of the body 12 toward its posterior side 32. This raised portion of the periphery 52 reduces risk of sub-luxation between the glenoid component 10 and the humeral head (natural or prosthetic) when the humeral head is articulated toward the raised portion of the periphery 52.

In some embodiments, the center of articulation 50 is offset by a distance dY between the center of articulation 50 and the mid-plane Y of at least 5%, from about 5% to about 10%, of at least 10%, or at least 20%, for example, of a maximum orthogonal distance DY between the mid-plane Y and the transverse projection of the body 12 relative to the axis Z. In some embodiments, the center of articulation 50 is offset by a distance dX between the center of articulation 50 and the mid-plane X of at least 5%, from about 5% to about 10%, of at least 10%, or at least 20%, for example, of a maximum orthogonal distance DX between the mid-plane X and the transverse projection of the body 12 relative to the axis Z.

Figure 4:
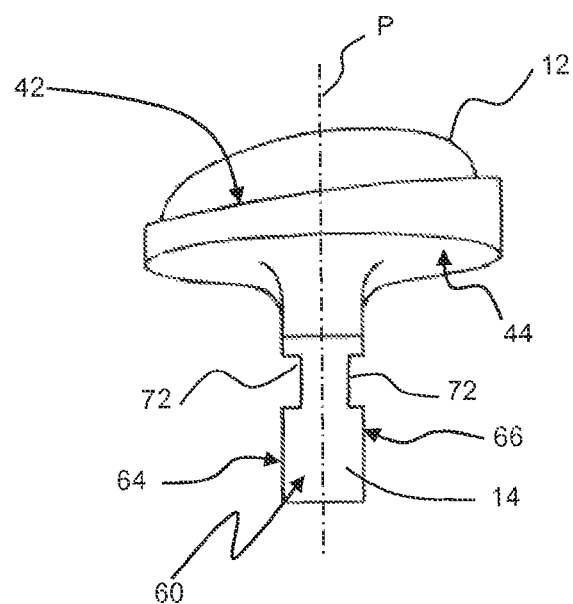
FIG. 4 is an elevation view of the glenoid component corresponding to perspective IV of FIG. 2, according to some embodiments.

As shown in FIGS. 1, 2, and 4, the anchor portion 14 is shaped as a fin, or keel, where the anchor portion 14 is substantially plate-shaped with a mid-plane P (FIG. 4) that extends transversely to the second surface 44 of the body 12. In some embodiments, the anchor portion 14 is sized, shaped, and/or otherwise configured to be embedded and immobilized in the glenoid cavity G and optionally includes features for promoting bone growth, or secondary attachment. As shown in FIG. 2, the anchor portion 14 defines a first end face 60 and a second end face 62 through which the mid-plane P passes (FIG. 4), as well as a first primary face 64 and a second primary face 66 (FIG. 4) positioned opposite to the first primary face 64. The anchor portion 14 also includes a through hole 70, as well as grooves 72 that optionally serve to form spaces for encouraging secondary fixation via bone ingrowth. In other embodiments, a primary peg (not shown) is used for the anchor portion 14, where the primary peg extends substantially coaxially with the axis Z.

As shown, the anchor portion 14 is centered on the axis Z of the mid-planes X, Y of the body 12, where the anchor portion 14 is implanted in the glenoid cavity in the direction of the axis Z. In some embodiments, the axis Z is central to the anchor portion 14, extending along the mid-plane P, and running substantially equidistant from the first and second end faces 60, 62, as well as the first and second primary faces 64, 66 of the anchor portion 14.

Some methods of implanting the glenoid component 10 and centering a humeral head on the glenoid component 10 include a surgeon exposing the glenohumeral joint, dislocating the humerus from the glenohumeral joint, forming or replacing the natural humeral head, forming the glenoid cavity G, implanting the glenoid component 10 into the glenoid cavity G along the axis Z, and articulating the humeral head with the glenoid component 10. In some embodiments, the glenohumeral joint is exposed using known techniques and the humerus is similarly dislocated from the glenoid G. The glenoid G is optionally formed or otherwise configured to receive the glenoid component 10.

In some embodiments, the glenoid component 10 is implanted into the glenoid G along the central axis Z such that the antero-posterior mid-plane X is oriented generally antero-posteriorly relative to the patient and the vertical mid-plane Y is oriented generally infero-superiorly relative to the patient. In some embodiments, the center of articulation 50 is thus offset in an inferior and anterior direction relative to the central axis Z following implantation in the glenoid G. As part of implantation, the anchor portion 14 is optionally embedded into a cavity or pocket formed into the bony structure of the glenoid G and the second surface 44 is received against bony structures of the glenoid G in a complementary fit.

In some embodiments, the humeral head is prepared (e.g., via forming procedure) to better articulate with the glenoid component 10 and/or a portion of the humerus (e.g., the proximal humeral head) is removed and replaced with an artificial humeral head. Regardless, in some embodiments, the humeral head is engaged with the first surface 42 such that the humeral head is seated against the apical portion of the articulation surface when the humeral head is in a neutral position, where the "neutral position" is meant to correspond to a position where the humerus is hanging freely at the patient's side.

In order to evaluate performance of the glenohumeral joint, the humeral head is articulated against the first surface 42 from the neutral position to a modified position (e.g., including flexion, extension, abduction, adduction, lateral rotation, and/or medial rotation) such that the humeral head transitions from the apical portion at the center of articulation 50 toward the raised part of the periphery 52 to assess a risk of luxation between the humeral head and the glenoid component 10 when the humeral head is moved toward the modified position.

If the assessment is unfavorable, the surgeon optionally replaces the glenoid component 10 with another glenoid component having a different offset between the center of articulation 50 and the central axis Z, a different amount of curvature for the first surface 42, and/or a differently sized glenoid component, for example. If the assessment is favorable, the surgeon closes the glenohumeral joint and evaluates the tension in the joint through a variety of positions, including at the neutral and modified positions. Generally, the modified position results in the humeral head being moved outwardly, away from the glenoid G which tightens the joint and avoids dislocation of the humeral head from the first surface 42, thereby reducing dislocation risk. In other words, the humeral head is engaged with a peripheral portion of the first surface 42 that is raised relative to the center of articulation 50 and offset from the central axis Z in an opposite direction than the center of articulation 50 such that the tension in the glenohumeral joint retaining the humeral head against the articulation surface 42 is increased.

Various modifications and additions can be made to the exemplary embodiments discussed without departing from the scope of invention. For example, various body shapes are contemplated, including substantially circular or irregular shapes, as well as various anchoring portions, including pegs, screws, and/or others. As used herein, the terms "upper," "lower," "front," "back," "left," "right," "top," "bottom," and the like are relative positional terms, used for description purposes, and are not to be taken in an overly limiting sense. While the embodiments described above refer to particular features, the scope of invention also includes embodiments having different combinations of features and embodiments that do not include all of the above described features.

The following is claimed:

1. A glenoid component comprising:
   a body forming an articulation surface configured for engaging a humeral head and an anchor surface configured for engaging a glenoid cavity of a shoulder, the body having an antero-posterior mid-plane, an infero-superior mid-plane orthogonal to the antero-posterior mid-plane, and a central axis at an intersection of the antero-posterior and infero-superior mid-planes, the articulation surface being substantially concave and defining a center of articulation and a first peripheral portion that is raised in the direction parallel to the central axis compared to a second peripheral portion, the first peripheral portion being disposed superiorly of the antero-posterior mid-plane, the second peripheral portion being disposed inferiorly of the first peripheral portion, the center of articulation being offset from both the antero-posterior and infero-superior mid-planes in a first direction from the central axis and the first peripheral portion being offset from the antero-posterior and infero-superior mid-planes in a second direction that is opposite to the first direction; and
   an anchor portion connected to the body and centered on the central axis, the anchor portion being configured for being embedded in a boney structure of the glenoid cavity.

2. The glenoid component of claim 1, wherein the anchor portion includes a keel structure centered on the antero-posterior-mid-plane and central axis.

3. The glenoid component of claim 1, wherein the center of articulation corresponds to an inferiorly and anteriorly offset position on the articulation surface.

4. The glenoid component of claim 1, wherein the articulation surface is substantially concave such that a humeral head is seated against the center of articulation of the articulation surface when the humeral head is in a neutral position.

5. The glenoid component of claim 1, wherein the center of articulation is offset, when implanted, in a lower, anterior direction relative to the central axis of the glenoid component such that a humeral head is seated against a lower, anterior portion of the articulation surface when the humeral head is in a neutral position.

6. The glenoid component of claim 1, wherein the anchor portion includes a keel centered on the central axis.

7. The glenoid component of claim 1, wherein the anchor portion includes a peg centered on the central axis.

8. A glenoid component comprising:
 a body and an anchor portion, the body defining an articulation surface and an anchor surface opposite the articulation surface, the body having an antero-posterior mid-plane, an infero-superior mid-plane orthogonal to the antero-posterior mid-plane, and a central axis at an intersection of the antero-posterior and infero-superior mid-planes;
 the anchor portion being centered on the body along the central axis of the body,
 wherein the articulation surface is curved and has a center of articulation that is offset from both the antero-posterior and infero-superior mid-planes in a first direction from the central axis of the body and a peripheral portion, the peripheral portion having a first zone and a second zone, each of the first and second zones raised in a direction parallel to the central axis compared to the center of articulation, the first zone being raised by an amount greater than the second zone, the first zone being offset from the antero-posterior mid-plane and the infero-superior mid-plane in a second direction from the central axis of the body, the second direction being opposite the first direction.

9. The glenoid component of claim 8, wherein the anchor portion comprises a keel centered on the central axis.

10. The glenoid component of claim 8, wherein the anchor portion extends along the infero-superior mid-plane.

11. The glenoid component of claim 8, wherein the anchor portion comprises a peg centered on the central axis.

12. The glenoid component of claim 8, wherein the center of articulation corresponds to an anteriorly offset position from the central axis of the body.

13. The glenoid component of claim 12, wherein the center of articulation corresponds to an inferiorly offset position from the central axis of the body.

14. A glenohumeral joint comprising:
 the glenoid component of claim 8; and
 an artificial humeral head.

15. A glenohumeral joint comprising:
 a glenoid component comprising an antero-posterior mid-plane, an infero-superior mid-plane orthogonal to the antero-posterior mid-plane, and an articulation surface having a center of articulation at least partially bounded by a first raised peripheral portion and a second raised peripheral portion, the center of articulation being offset from both the antero-posterior and infero-superior mid-planes in a first direction from a central axis of the glenoid component, the central axis being defined at an intersection of the antero-posterior mid-plane and the infero-superior mid-plane, the first raised peripheral portion being offset from the antero-posterior mid-plane and the infero-superior mid-plane in a second direction that is opposite the first direction;
 the second raised peripheral portion being raised by an amount less than the first peripheral portion;
 wherein a first, neutral position of the glenohumeral joint can be provided in which a humeral head is positioned against the center of articulation of the glenoid component; and
 wherein a second position of the glenohumeral joint can be provided in which a humeral head is engaged with the first raised peripheral portion, the second position causing a tension in the glenohumeral joint retaining the humeral head against the articulation surface.

16. The glenohumeral joint of claim 15, further comprising an artificial humeral head.

17. The glenohumeral joint of claim 15, wherein the center of articulation corresponds to an anteriorly offset position from the central axis of the glenoid component.

18. The glenohumeral joint of claim 17, wherein the center of articulation corresponds to an inferiorly offset position from the central axis of the glenoid component.

\* \* \* \* \*